United States Patent [19]

Wijay et al.

[11] Patent Number: 4,921,483
[45] Date of Patent: May 1, 1990

[54] ANGIOPLASTY CATHETER

[75] Inventors: Bandula Wijay, Webster; Paolo Angelini, Houston, both of Tex.

[73] Assignee: Leocor, Inc., Webster, Tex.

[21] Appl. No.: 100,363

[22] Filed: Sep. 23, 1987

Related U.S. Application Data

[63] Continuation-in-part of Ser. No. 811,162, Dec. 19, 1985, abandoned.

[51] Int. Cl.$^5$ .............................................. A61M 29/02
[52] U.S. Cl. ........................................ 604/96; 606/194
[58] Field of Search ...................... 604/95–103, 604/280, 4, 266; 128/344, 348.1, 656–658, 672–675

[56] References Cited

U.S. PATENT DOCUMENTS

| | | |
|---|---|---|
| 3,434,869 | 3/1969 | Davidson ............................ 604/266 |
| 3,435,826 | 4/1969 | Fogarty ............................. 128/348.1 |
| 3,605,725 | 9/1971 | Bentov .............................. 604/95 X |
| 3,671,490 | 5/1972 | Bargain ................................ 260/47 |
| 3,833,004 | 9/1974 | Vasquez et al. .................... 128/349 |
| 3,834,394 | 9/1974 | Hunter et al. ...................... 128/325 |
| 3,890,976 | 6/1975 | Bazell et al. ...................... 604/96 X |
| 4,024,873 | 5/1977 | Antoshkiw et al. ................ 128/349 |
| 4,024,875 | 5/1977 | Antoshkiv et al. .................. 604/96 |
| 4,029,104 | 6/1977 | Kerber ................................. 604/96 |
| 4,154,244 | 5/1979 | Becker et al. ...................... 128/349 |
| 4,191,193 | 3/1980 | Seo ..................................... 128/675 |
| 4,254,774 | 3/1981 | Boretos . |
| 4,271,839 | 6/1981 | Fogoarty et al. ................... 128/344 |
| 4,292,947 | 10/1981 | Tanasawa . |
| 4,299,226 | 11/1981 | Banka ................................. 128/349 |
| 4,307,732 | 12/1981 | Evans . |
| 4,318,410 | 3/1982 | Chin . |
| 4,323,071 | 4/1982 | Simpson et al. ................... 604/98 X |
| 4,326,532 | 4/1982 | Hammar ............................. 604/266 |
| 4,327,709 | 5/1982 | Hanson et al. ........................ 128/1 |
| 4,385,635 | 5/1983 | Ruiz .................................... 128/658 |
| 4,411,055 | 10/1983 | Simpson et al. ..................... 29/447 |
| 4,413,989 | 11/1983 | Schjeldahl et al. .................. 604/96 |
| 4,445,892 | 5/1984 | Hussein et al. ..................... 604/101 |
| 4,464,176 | 8/1984 | Wijayarathna . |
| 4,467,790 | 8/1984 | Schiff . |

(List continued on next page.)

FOREIGN PATENT DOCUMENTS

| | | |
|---|---|---|
| 87113702.2 | 9/1987 | European Pat. Off. . |
| 654214A | 2/1986 | Fed. Rep. of Germany . |
| PCT/DK86/-00083 | 7/1986 | PCT Int'l Appl. . |
| 0654214 | 12/1981 | Switzerland ...................... 128/344 |
| 1566674 | 5/1980 | United Kingdom . |
| 2172205 | 3/1986 | United Kingdom . |

OTHER PUBLICATIONS

Percutaneous Transluminal Angioplasty: General Principles, by Christos A. Athanasoulis, Nov. 1980.
Distal Hemoperfusion During Percutaneous Transluminal Coronary Angioplasty by Paolo Angelini, MD, Macques Heibig, MD and D. Richard Leachman, MD 8/1/86.
The Condensed Chemical Dictionary; 3rd Ed.; Hawley, p. 833.

Primary Examiner—Dalton L. Truluck
Assistant Examiner—Denise W. DeFranco
Attorney, Agent, or Firm—Steve Rosenblatt

[57] ABSTRACT

An angioplasty catheter has an elongated body with at least one lumen extending therethrough. A tip, constructed of materials softer than the elongated body is attached to the distal end of the body. The tip segment has at least one lumen passing therethrough which is in alignment withthe lumen in the elongated body. A guide is adapted to pass through the aligned lumens. A balloon is connected to the distal segment of the elongated body over its outer periphery, thereby creating a balloon cavity therebetween. At least one additional lumen is provided in the elongated body in flow communication with the balloon cavity, for selective inflation and deflation thereof, with a contrast fluid.

85 Claims, 6 Drawing Sheets

U.S. PATENT DOCUMENTS

| | | | |
|---|---|---|---|
| 4,490,421 | 12/1984 | Levy . | |
| 4,517,979 | 5/1985 | Pecenka | 128/325 |
| 4,526,175 | 7/1985 | Chin et al. | 128/344 |
| 4,531,512 | 7/1985 | Wolvek et al. | 128/344 X |
| 4,531,943 | 7/1985 | Van Tassel et al. | 604/280 |
| 4,536,179 | 8/1985 | Anderson et al. | 604/266 |
| 4,571,240 | 2/1986 | Samson et al. | 604/96 |
| 4,572,186 | 2/1986 | Gonld et al. | 128/341 |
| 4,573,470 | 3/1986 | Samson et al. | 604/344 |
| 4,577,637 | 3/1986 | Mueller, Jr. | 128/658 |
| 4,581,017 | 4/1986 | Sahota | 604/102 |
| 4,582,181 | 4/1986 | Samson . | |
| 4,583,974 | 4/1986 | Kokernak . | |
| 4,587,975 | 5/1986 | Salo et al. . | |
| 4,589,412 | 5/1986 | Kensey | 128/304 |
| 4,597,755 | 7/1986 | Samson et al. | 604/103 X |
| 4,601,706 | 7/1986 | Aillon | 604/122 |
| 4,616,648 | 10/1986 | Simpson | 128/303 |
| 4,616,653 | 10/1986 | Samson et al. | 128/344 |
| 4,621,646 | 11/1986 | Bryant | 128/692 |
| 4,650,466 | 3/1987 | Luther . | |
| 4,664,113 | 5/1987 | Frisbie et al. | 128/344 |
| 4,676,249 | 6/1987 | Arenas et al. | 128/657 |
| 4,692,148 | 9/1987 | Kantrowitz et al. | 604/96 |
| 4,702,252 | 10/1987 | Brooks et al. | 428/344 |
| 4,738,666 | 4/1988 | Fuqua | 604/280 |
| 4,744,366 | 5/1988 | Jang | 128/344 |
| 4,748,982 | 6/1988 | Horzewski et al. | 128/344 |
| 4,748,984 | 6/1988 | Patel | 128/658 |
| 4,754,752 | 7/1988 | Ginsburg et al. | 128/303 |
| 4,762,129 | 8/1988 | Bonzel | 128/344 |
| 4,763,654 | 8/1988 | Jang | 128/344 |
| 4,771,776 | 9/1988 | Powell et al. | 128/344 |
| 4,771,777 | 9/1988 | Horzewski et al. | 128/344 |
| 4,771,778 | 9/1988 | Mar | 128/344 |
| 4,773,901 | 9/1988 | Norton | 604/265 |
| 4,775,371 | 10/1988 | Mueller, Jr. | 604/280 |
| 4,777,951 | 10/1988 | Cribier et al. | 128/344 |
| 4,782,834 | 11/1988 | Maguire et al. | 604/96 |
| 4,796,629 | 1/1989 | Grayzel | 128/344 |
| 4,798,586 | 1/1989 | Stevens | 604/96 |
| 4,808,164 | 2/1989 | Hess | 604/95 |
| 4,811,737 | 3/1989 | Rydell | 128/344 |
| 4,820,270 | 4/1989 | Hardcastle et al. | 604/96 |
| 4,821,722 | 4/1989 | Miller et al. | 128/344 |
| 4,824,436 | 4/1989 | Wolinsky | 604/53 |

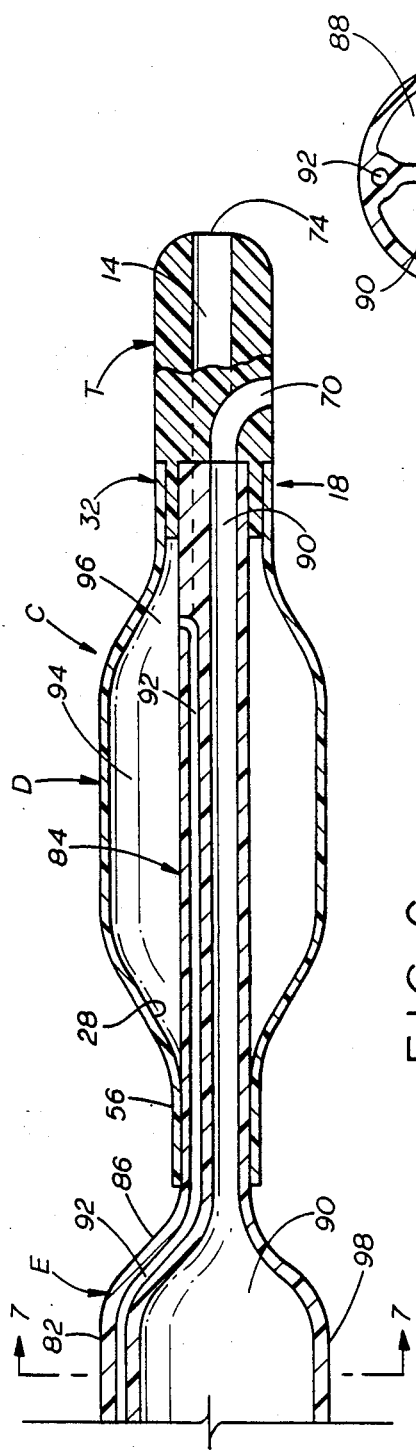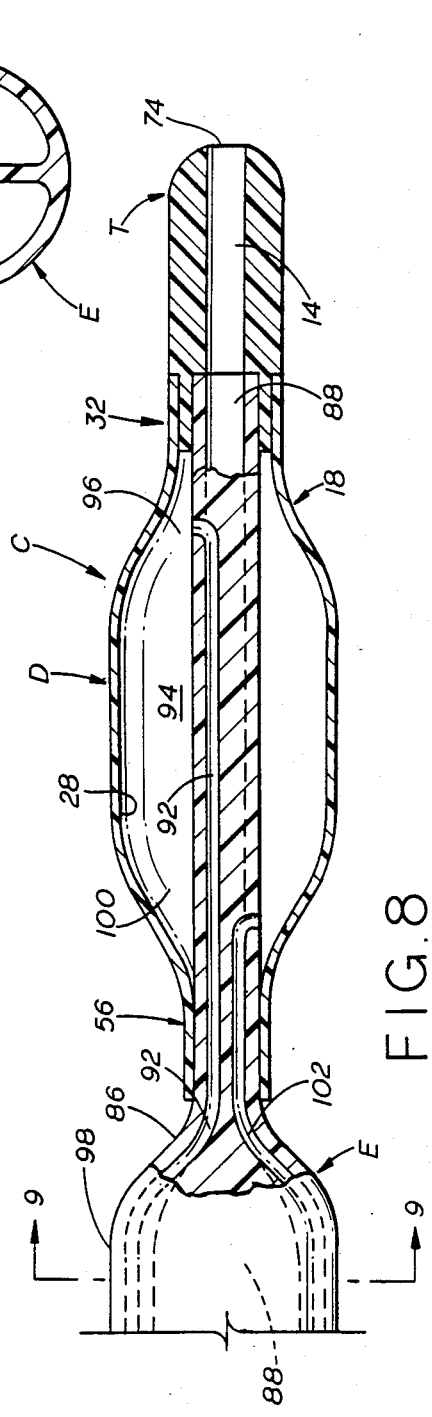

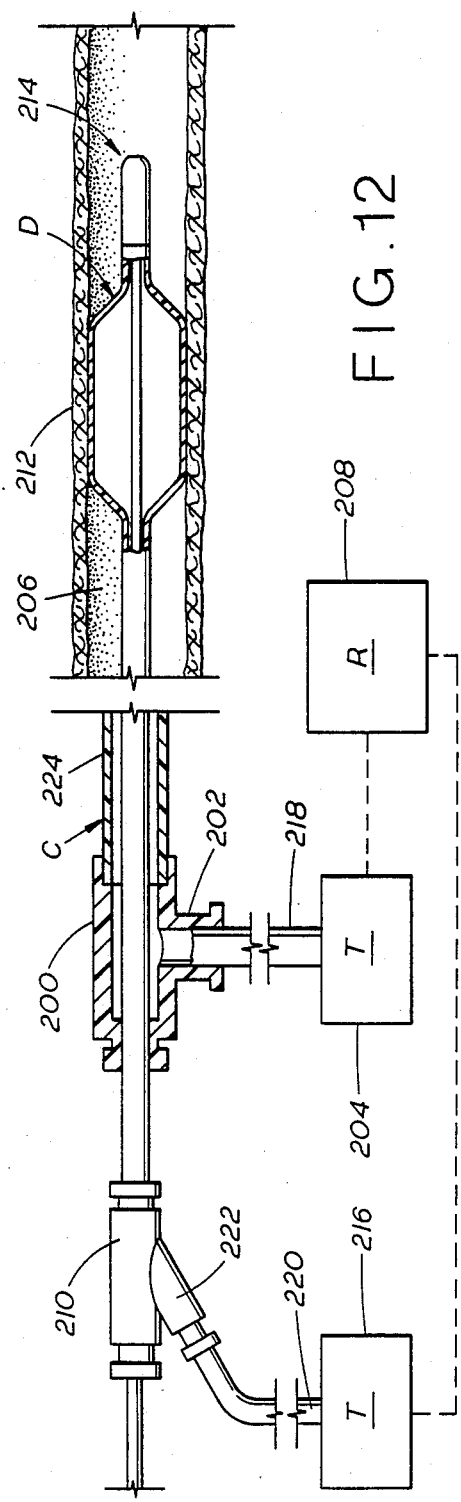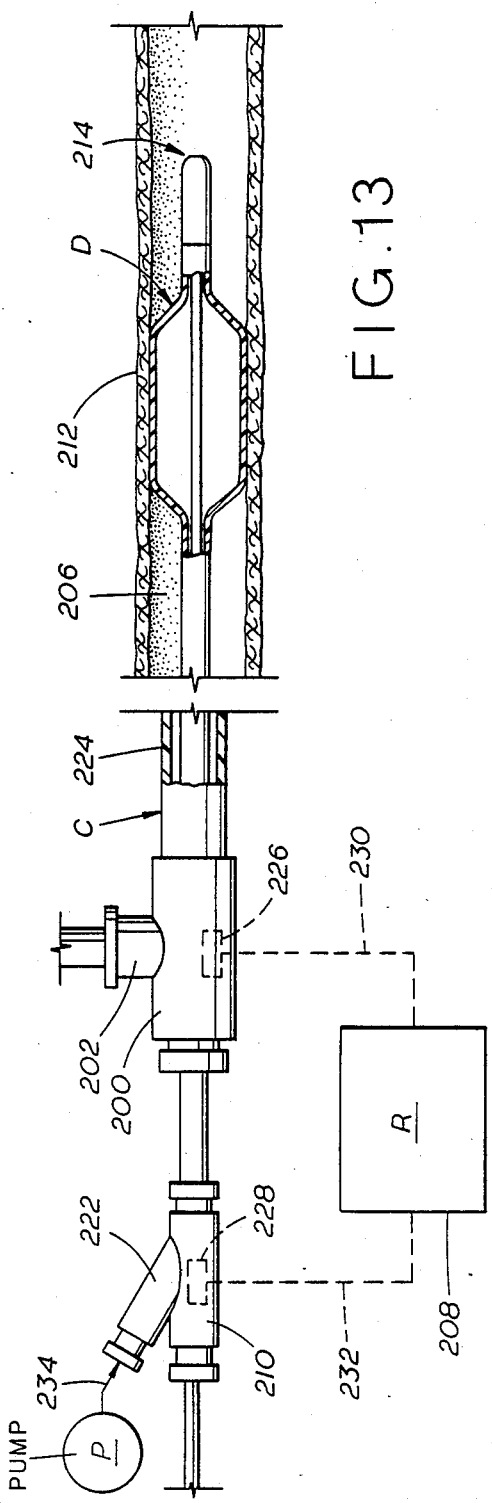

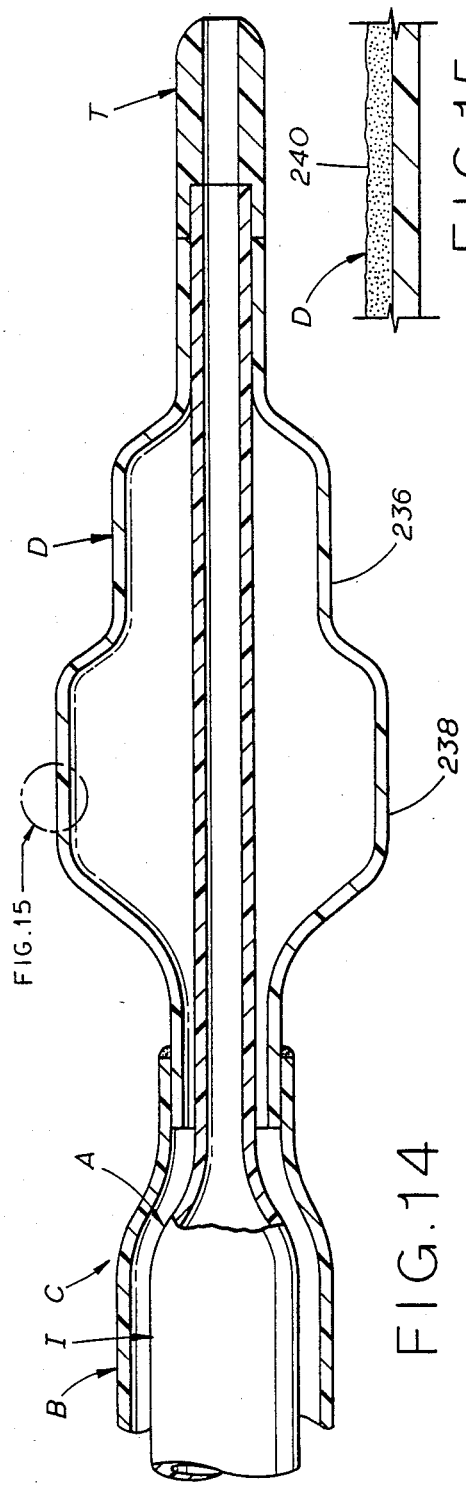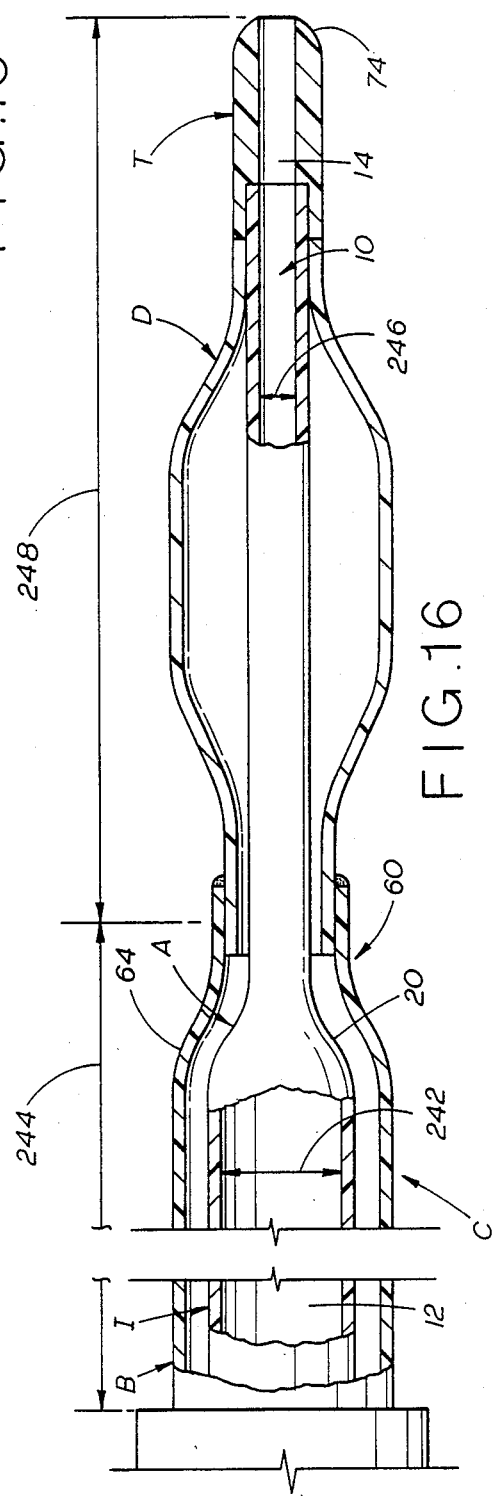

ANGIOPLASTY CATHETER

This is a continuation-in-part of co-pending application Ser. No. 811,162, filed on Dec. 19, 1985, now abandoned.

FIELD OF THE INVENTION

The invention relates to the field of surgery, and more particularly to instruments for facilitating the performance of surgical procedures involving the flow of blood. This technique has been generally described as percutaneous transluminal angioplasty.

BACKGROUND OF THE INVENTION

Obstructive coronary artery disease is generally regarded as a serious health problem in the United States and most of the western world. When drug treatment fails or inadequately controls angina pectoris, coronary artery bypass graft surgery is generally used. In 1964 a translumenal coaxial catheter dilation method for dilating atheromatous lesions in peripheral arteries was introduced by Dotter and Judkins. This technique required sequential dilation of stenotic lesions and employed progressively larger dilating catheters. Subsequently in 1971 a "Fogarty balloon catheter" was used to perform translumenal arteriolplasty. Subsequently, Gruntzig employed earlier techniques using a single double lumen catheter with a nondistensible balloon segment at its tip which was positioned in the lumen at the stenotic segment of a peripheral artery. The elastic balloon segment was then inflated, resulting in compression of the atheromatous lesion in a manner perpendicular to the vessel, thus dilating the lumen. The balloon remained inflated for ten to fifteen seconds at seven atmospheres internal pressure and was then deflated. As a result, there was a significant reduction in complications due to endothelial damage, such as that caused by earlier known coaxial translumenal dilation technique and thus a marked improvement in vessel patency through the use of the Gruntzig catheter was achieved.

In earlier designs, the amount of pressure which could be applied through a balloon type expander was limited and thus insufficient to dilate certain stenotic lesions. This shortcoming was due to the use of polyvinylchloride balloons which had structural limitations that limited internal pressures to approximately seven atmospheres.

Other catheter designs resulted in a total cessation of blood flow distal to the site of the treatment. Studies in living dogs with normal coronary arteries have shown that coronary translumenal angioplasty may be associated with brief, self-limited ventricular tachycardia. During the inflation of the balloon, distal coronary pressure falls to zero. Because of the lack of blood flow and the pressure distal to the treatment site the period of use such known catheters must be relatively short to prevent complications due to the lack of blood supply. This limitation on inflation time tended to reduce the success rate of the coronary translumenal angioplasty.

The translumenal coronary angioplasty technique consists of a catheter system introduced via the femoral artery under local anesthesia. A preshaped guiding catheter is positioned into the orifice of the coronary artery and through this catheter a second dilation catheter is advanced into the branches of the coronary artery. The dilation catheter had an eliptical shape distensible balloon portion near its tip which could be inflated and deflated. After traversing the stenotic lesion of the coronary artery, the distensible portion was inflated with fluid which compressed the atherosclerotic material in a direction generally perpendicular to the wall of the vessel thereby dilating the lumen of the vessel. Peripheral arterial lesions treated by this technique have demonstrated that the atheroma can be compressed leaving a smooth luminal surface. Studies have shown that the patency rate two years following the dilation of the iliac and femoropopliteal atherosclerotic lesions was greater than seventy percent.

Although guiding catheters are used in placement of angioplasty (dilation) catheters, the angioplasty catheter can be placed in a stenotic lesion using solely the wire guide if the lesion is proximately located to the point of entry in the body. The word "guide" as referred to in this application is directed to both wire guides and guiding catheters separately or as used in tandem. Typically a guide of appropriate size is advanced through the stenotic lesion and the balloon catheter is threaded over it and advanced to the area of the stenosis. Once the area of the stenosis is reached, the balloon in the catheter is inflated to a high pressure depending on the size of the balloon and the type of stenosis, and the pressure is held for a period of time. During the procedure the distal and proximal pressure is measured to evaluate the physiological conditions of the organ. More specifically, the pressure differential is measured after deflating the balloon and is used as an indication of the degree of dilation achieved.

Past designs have employed a stiff catheter tip on the angioplasty catheter which often resulted in pulling the guide out of the stenoic lesion as the catheter was advanced toward the lesion. Separately, in using the angioplasty catheter, it was often necessary to measure the pressure distal to the catheter. Past designs employed a guide closely fitting to the internal cross section of the distal lumen in the catheter thereby making it difficult to obtain adequate pressure measurements due to the large pressure drops involved as a result of the usage of close clearances. The pressure measurements were of the nature of a dynamic measurement, the accuracy and frequency response of which was greatly and adversely affected by the pressure drops within the catheter measurement lumen. It was frequently required that the guide be retracted and replaced in order to achieve accurate pressure measurement.

The use of angioplasty catheters often made it necessary to infuse drugs or oxygenated blood, distal to the stenosis to provide adequate physiological function of the organ in question. Past designs did not provide for such a separate lumen to carry drugs necessary to prevent undue contractions of the arterial wall as a result of the insertion of the angioplasty catheter. To the extent such drugs were necessary to relax the arterial wall, the lumen through which the guidewire passed served the auxillary function of a drug injection port. However, usage of the same lumen for pressure measurement as well as infusion of drugs or other fluids impeded the ability to maintain continuous and accurate pressure measurements.

Angioplasty catheters used in the past had relatively large catheter body diameters which tended to occlude the artery of concern causing reduced blood flow to the lesion or the organ it supplies. One such catheter is disclosed in U.S. Pat. No. 4,323,071 (FIG. 4). Other catheters although using a tapered body, employed a rigid tip which, if the arterial path was particularly tortuous, tended to pull the guide wire from the stenosis. One such catheter is disclosed in U.S. Pat. No. 4,413,989 (FIG. 8).

Flexible tips attached to the distal end of an angioplasty catheter have been used to inject radiopaque contrast or medicaments into the femoral artery as part of diagnostic or treatment procedures. Such deformable tips had the object of preventing punctures of the wall of the aorta and have been provided to have a larger cross-sectional profile than the catheter body to which they are attached. Some designs even featured means to inflate the deformable tip to increase the contact area between the tip and the body tissue to reduce the pressure per unit area applied to the tissue. One such design is disclosed in U.S. Pat. No. 4,531,943.

In past designs it was often difficult to estimate the location of the tip of the catheter. Prior designs employed the use of a gold band near the distal end of the catheter thereby making that portion of the catheter visible under an x-ray machine. However, because it was risky to attach such rings at the extreme distal end of the catheter, the extreme distal tip of the catheter was not visible under x-ray and often the physician performing the procedure had to guess as to its location. This shortcoming of past catheters has been addressed in the catheter of the present invention by the provision of a radiopaque tip.

Known angioplasty catheters have dilation balloons attached to the catheter body by adhesives or by heat sealing. Most often, these balloons are made out of polyvinylchloride or irradiated polyethylene. Polyvinylchloride balloons are normally solvent or adhesive bonded to catheter bodies of the same material and polyethylene balloons are adhesive bonded or heat shrunk to catheter bodies of the same material, or a blend of polyethylene and polypropylene, so as to obtain catheter body stiffness. Most such catheters have relatively stiff tips at their distal end which often causes the preplaced guide to be pulled out of the lesion area during catheter advancement in tortuous arteries as well as intimal damage. Known catheters also contain relatively stiff bodies to carry the balloon adjacent the distal end of the catheter. The stiffness of the catheter body continues in the area of the balloon up to the distal end of the catheter.

Known catheters contain balloon lumen bleed holes whereby air can be removed directly out of the balloon cavity and out of the catheter during the filling of the balloon. These additional lumens either in the form of small metal tubes or as a multilumen catheter tube, consumed valuable cross-sectional area of the catheter tube that otherwise could be used for other purposes such as pressure measurements.

Known catheter designs have employed an inner and outer tube wherein the outer tube contains the balloon as an integral portion thereof or a separate balloon which is bonded to the outer tube. The annulus between the inner and outer tubes is used for inflation of the balloon.

Known angioplasty catheters have been shipped in a sterilized condition to doctors and hospitals with the balloon in a deflated condition and having gas entrained therein. Prior to using such catheters, doctors or technicians had to inject a contrast fluid into the balloon to displace the gases therein. This procedure involved sequential filling and evacuation of balloon using a plunger connected to the proximal end of the catheter. Such catheters were shipped to doctors and hospitals with the balloon in a wing-folded condition. Essentially wing folding involved flatening of the balloon along the catheter body and folding the balloon over onto the catheter body in two segments which resemble wings coming from a fuselage. In the past, the catheters were wing-folded in the factory prior to shipment. However, in order to remove the entrained gases, the doctor or technician had to unfold the wings and fill the balloon with contrast fluid while evacuating gases therefrom. As a result, the advantage of the balloon tending to retain its wing-folded position after shipment was lost. The doctor or technician after filling the balloon with contrast fluid had to again attempt to manipulate the balloon with his or her fingers to reachieve the wing-folded position which reduced the profile of the catheter.

The catheter of the present invention addresses this problem by prefilling the catheter with contrast fluid and placing a sleeve over the balloon after it has been wing-folded. Accordingly, the advantage of the wing-folding is retained and the doctor merely removes the sleeve and the sterile catheter is ready for insertion, with the balloon in a low profile position.

It is an object of this invention to provide a soft atraumatic catheter tip in which radiopaque fillers such as bismuth-oxychloride or bismuth-subcarbonate are incorporated.

It is an object of the invention to provide a relatively soft catheter tip to minimize the tendency of the catheter to dislocate a guide out of a stenosis when the catheter is advanced in a tortuous path, and also minimize intimal damage.

It is another object of this invention to provide a catheter tip which can be insert molded, heat bonded, or adhesive bonded to the relatively stiff catheter body proximal to it. It is a further object of this invention to use material such as nylon, polyvinylchloride, polyurethane, of different stiffnesses that are readily bondable using the aforementioned methods.

It is a further object of this invention to provide an inner tube that is relatively large in its internal diameter and that is necked down in the region of the balloon and for several centimeters proximal to the balloon in order to provide a large lumen for pressure measurement. The catheter provides an improved frequency response without sacrificing the total overall outside diameter and maintaining a relatively small diameter in the region of the balloon thereby maintaining a low profile catheter design.

It is a further object of this invention in one of its alternate embodiments to provide a bleed lumen to bleed gases out of the balloon wherein the lumen extends within the wall of the outer tube thereby avoiding sacrificing any of the catheter cross-sectional area for other lumens thereby allowing such other lumens to be of maximum cross-sectional area within a low profile catheter.

It is a further object of this invention to provide, in one embodiment, an opening into the balloon cavity at its extreme distal end thereby facilitating the removal of gases during filling with contrast fluid.

SUMMARY OF THE INVENTION

An angioplasty catheter has an elongated body with at least one lumen extending therethrough. A tip, constructed of materials softer than the elongated body is attached to the distal end of the body. The tip segment has at least one lumen passing therethrough which is in alignment with the lumen in the elongated body. A guide is adapted to pass through the aligned lumens. A balloon is connected to the distal segment of the elongated body over its outer periphery, thereby creating a balloon cavity therebetween. At least one additional lumen is provided in the elongated body in flow communication with the balloon cavity, for selective inflation and deflation thereof, with a contrast fluid.

BRIEF DESCRIPTION OF THE DRAWINGS

FIG. 6 is a sectional elevational view of an alternative embodiment of the catheter;

FIG. 7 is a section through lines 7—7 of FIG. 6;

FIG. 8 is an sectional elevational view of an alternative embodiment of the catheter;

FIG. 12 is a schematic representation of an angioplasty catheter showing pressure measurement techniques using externally mounted transducers;

FIG. 13 is a schematic representation of an angioplasty catheter illustrating placement of pressure sensing transducers on the catheter.

FIG. 14 is a sectional view of the distal end of one embodiment of an angioplasty catheter illustrating a two stage balloon;

FIG. 15 is a detailed sectional view of the area shown in the dashed circle in FIG. 14;

FIG. 16 is a representation of an angioplasty catheter as shown in FIG. 1 illustrating several unique dimensional relationships therein.

DETAILED DESCRIPTION OF THE PREFERRED EMBODIMENT

Figure 1:
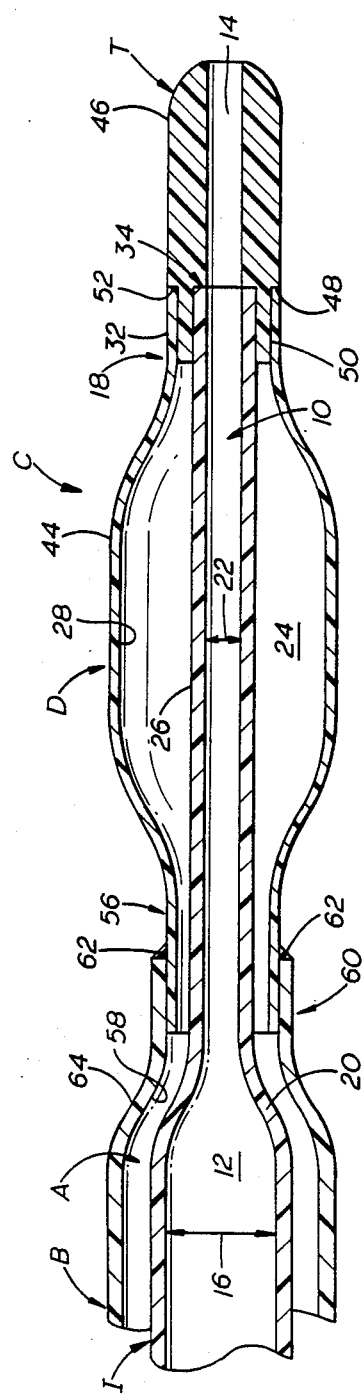
FIG. 1 is a sectional elevational view of one embodiment of the catheter of the present invention employing a coaxial design and having a tip with an outside shoulder.

The catheter C of the present invention has several embodiments described hereinbelow and illustrated in the figures. FIG. 1 illustrates a coaxial design for a catheter having an inner body member I, an outer body member B. Annulus A is defined between inner body member I and outer body member B. A tip T is connected to inner body member I. A balloon D is connected to outer body member B on one end and adjacent the distal end 10 of inner body member I.

Figure 2:
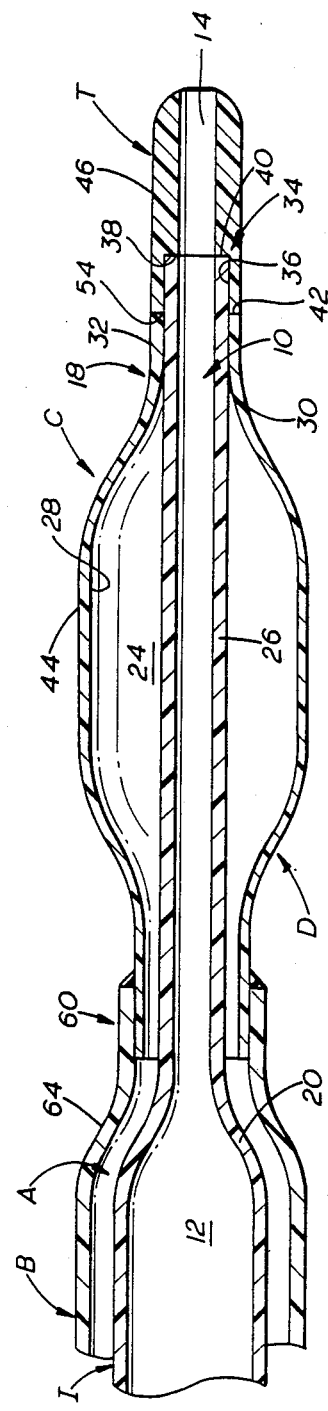
FIG. 2 is a sectional elevational view of the coaxial design as shown in FIG. 1 with an alternative balloon mounting.

As shown in FIG. 1, inner body member I has at least one lumen 12 therein and extending therethrough. Tip T has an axial lumen 14 which is aligned with lumen 12 when tip T is affixed to distal end 10 of inner body member I. As seen in FIGS. 1 and 2, inner body member I extends beyond outer body member B. As previously stated, one of the objectives of the catheter C of the present invention is to provide for a low profile without, at the same time affecting the sensitivity of dynamic pressure measurements within the artery in question. To this end, lumen 12 has a relatively large cross-sectional area as shown by arrow 16 for substantially the entire length of the catheter. However, in order to avoid impeding the blood flow into the stenotic region in which the angioplasty procedure is to take place, it is desirable to have the distal end 18 of the catheter assembly C as small as possible to avoid interruption of blood flow. Accordingly, inner body member I has a tapered segment 20 which in effect necks down the cross-sectional area of lumen 12 from the section as shown by arrow 16 to a smaller cross-sectional area shown by 22.

As shown in FIG. 1, balloon D, which is preferably constructed of polyethylene or polyester, has an elongated shape which defines an annular cavity 24 between the outer surface 26 of inner body member I and the inner surface 28 of balloon D. Cavity 24 is in flow communication with annulus A. Cavity 24 is capped off at its distal end 30 (FIG. 2) in one of several alternative methods. In the first alternative, balloon D has a distal neck 32 which is bonded, sealed or otherwise joined, using methods known in the art, to the outer surface 26 of inner body member I. Tip T has an internal mounting shoulder 34 (FIG. 2) which includes annular surface 36 and radial surface 38 adjacent thereto. Tip T is butted against the distal surface 40 of inner body member I as can readily be seen in FIG. 2. Tip T is secured to inner body member I, by methods known in the art on at least two adjacent surfaces: to wit, 36 and 38. Tip T can be further secured to the catheter C by connecting distal neck 32 of balloon D to radial surface 42 of balloon D. With the above-described arrangement, the distal end 18 (See FIG. 1) of the catheter C maintains a low profile as the outer surface 44 of balloon D at distal neck 32 is maintained substantially flush to the outer surface 46 of tip T.

Alternatively, as shown in FIG. 1, tip T can have the same internal shoulder design 34 as illustrated in FIG. 2. In the alternative design shown in FIG. 1, tip T has an external mounting shoulder 48 which has a annular surface 50 and a radial surface 52 adjacent thereto. Distal neck 32 of balloon D is secured to annular surface 50 and radial surface 52 of tip T. The connection method illustrated in FIG. 1 provides additional security in mounting of tip T in that apart from contact between inner body member I and annular surface 36 and radial surface 38, of internal mounting shoulder 34, additional mounting points exist due to the bond between distal neck 32 and external mounting shoulder 48. It is to be understood that distal neck 32 can be secured to external mounting shoulder 48 by various means known in the art. Similarly, shoulder 34 can be secured to inner body member I by known means. The mounting method illustrated in FIG. 1 results in outer surface 44 of balloon D adjacent neck 32 being flush with outer surface 46 of tip T. However, due to the use of the external shoulder, the profile of catheter C as illustrated in FIG. 1 is slightly larger than the profile illustrated in FIG. 2.

Figure 4:
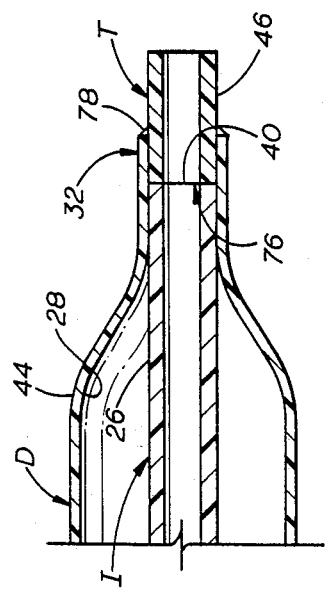
FIG. 4 is a sectional elevational view of an alternative mounting of the distal end of the balloon.

FIG. 4 illustrates yet another alternative embodiment for securing tip T to the distal end 40 of inner body member I. Tip T is preferably melt bonded to distal end 40 and has an outer periphery similar to outer surface 26 of inner body member I. Accordingly, outer surface 46 of tip T is aligned with outer surface 26 of inner body member I. The distal neck 32 of balloon D spans the melt bonded joint 76 between tip T and inner body member I. A tapered transition 78 is provided between outer surface 44 of balloon D and outer surface 46 of tip T, to avoid damage to the arterial wall during insertion and removal of the catheter C. The inner surface 28 of balloon D is preferably connected to both the outer surface 26 of inner body member I and the outer surface 46 of tip T by known methods. Alternatively, inner surface 28 may be joined solely to outer surface 46 although it may also contact surface 26. As a result, the distal neck 32 secures tip T to inner body member I, annularly with tip T also connected to inner body member I along matched radial surfaces making up joint 76. The arrangement shown in FIG. 4 also presents a low profile for the catheter C while adding the advantages of a flexible tip to counteract the tendency of an otherwise stiff catheter to dislocate the guide from the stenosis where a particularly tortious arterial path must be negotiated to reach the stenosis.

Experience has shown that distal neck 32 of balloon D can be fabricated to be 0.004 inches thick. The proximal end 54 (FIG. 2) of tip T can also be manufactured to the same thickness which results in a smooth transition between the balloon D and the tip T with a minimal increase in the profile of the catheter.

In order to further decrease the profile of the catheter, and thus facilitate blood flow to the lesion when the distal end of the catheter is moved toward the stenosis, the proximal neck 56 of balloon D is secured to the inner surface 58 of outer body member B adjacent distal end 60 of outer body member B. A buffed and smoothened edge 62 is used adjacent outer surface 44 of balloon D adjacent distal end 60 of outer body member I. The use of the smoothed edge 62 which has a slight taper thereon, eliminates any sharp edges which could irritate or tear through the arterial wall on insertion or removal of the catheter C. As can readily be seen from examining FIGS. 1 and 2 when balloon D is deflated, the maximum profile of the distal end 18 of catheter C is represented by the diameter of tip T (surface 46) as measured in a plane perpendicular to the longitudinal axis of catheter C.

The flexibility of the catheter C may be adjusted in several ways. One way to affect the relative stiffness of the distal end 18 of catheter C, which extends from the distal end 60 of the outer body member B to the end of tip T, is to vary the length of proximal neck 56 of balloon D. The neck 56 can be varied from 1-60 mm, by example and not by way of limitation. Along the same lines, the overall length of tip T can be adjusted to affect the bendability of the assembly of the catheter C. Another way to affect the overall stiffness of the distal end 18 of catheter C is to prepare the formulation of inner body member I and tip T to varying hardnesses. Typically, by example and not by way of limitation, the tip T can be in the range of 50 to 90 A hardness as measured by the Shore method and can be made from a material such as nylon. The inner body member I, by example and not by way of limitation, can be made of a stiffer grade of nylon such as approximately 140 on the Rockwell scale. The relative hardnesses of the tip T and the inner body member I can be adjusted in conjunction with adjustments of the length of proximal neck as well as the overall length of tip T to achieve the desired stiffness of catheter C for a particular application. Typically, tip lengths can be in the range of one to thirty millimeters, by example and not by way of limitation although a range of 1-10 mm. is preferred. Similarly, proximal neck 56 can be provided in varying lengths in the range of one to six centimeters, by example and not by way of limitation.

Figure 3:
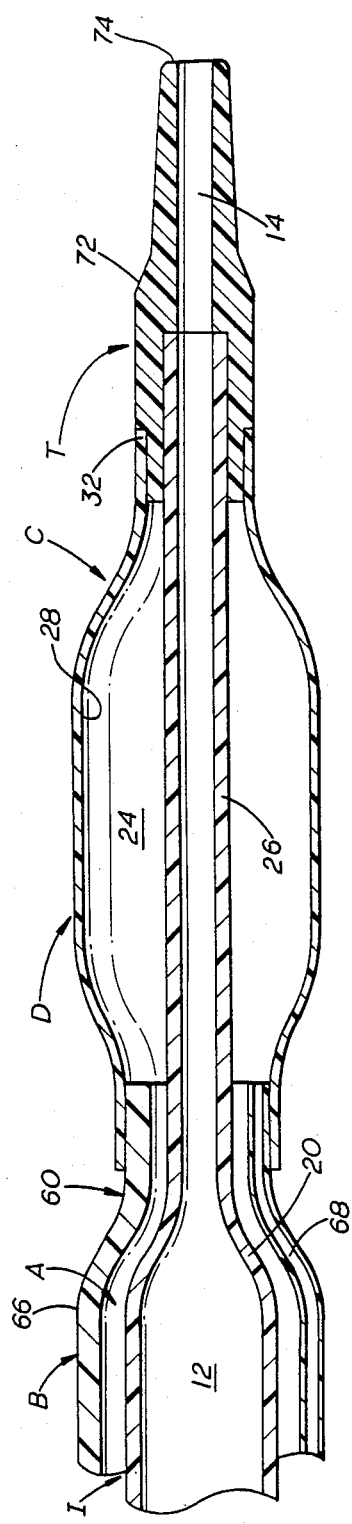
FIG. 3 is a sectional elevational view of the coaxial design of FIG. 1 showing an alternative mounting of the proximal end of the balloon.
Figure 5:
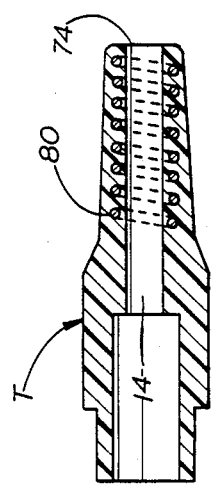
FIG. 5 is a sectional elevational view of an embodiment, of the tip showing a spring embedded therein.

As an alternative way to modulate the relative stiffness of the distal end 18 of the catheter C, FIG. 5 illustrates the tip T in the embodiment illustrated in FIG. 3 with an embedded coil spring 80 mounted toward the most distal end 74 of tip T. As shown in FIG. 5, spring 80 circumscribes the lumen 14 extending through the tip T. The length and spring rate of spring 80 can be adjusted depending on the desired stiffness. However, the overall profile of the tip must be retained at a level as small as possible. It should be noted that when using spring 80 embedded in tip T an infusion lumen 70 as disclosed in FIG. 6 is generally not used.

As seen in FIGS. 1 and 2, annulus A has a substantially constant cross-section proximally and distally to tapered segment 20 on inner body member I. This is accomplished by a taper 64 on outer body member B adjacent to its distal end 60. Taper 64 is aligned with tapered segment 20 of inner body member I. A suitable contrast fluid (not shown) is inserted into annulus A from the proximal end of the catheter C (not shown) to fill up cavity 24 thereby inflating the balloon and exerting radial forces against the stenosis.

The low profile of the catheter C of the present invention as shown in FIGS. 1 and 2 is significant in permitting continual blood flow while the catheter C is inserted into an artery such as the coronary artery. The low profile of the catheter of the present invention presents an improvement over other known designs in that the low profile permits continued blood flow as the catheter C is inserted into the artery while at the same time, catheter C of the present invention permits sensitive pressure measurements during the angioplasty procedure. Since measurement of pressure is a dynamic type of measurement, it is significant not to increase the flow resistance in lumens 12 and 14. A substantially smooth wall in lumens 12 and 14 can reduce such resistance to flow.

As shown FIGS. 1 and 2, a guide must pass through aligned lumens 12 and 14. The necking down of lumen 12 to the cross-section depicted by arrow 22 acts to increase the flow resistance thereby tending to make pressure measurements more difficult. However, this section of lumen is of relatively short length and necessary in order to achieve the low profile nature of the distal end 18 of catheter C. Transitions 20 and 64 allow the cross-sectional area of lumen 12 to increase in size, measured in a proximal direction, as soon as is possible. As a result the overall flow resistance of lumens 12 and 14 is kept to a minimum which in turn increases the sensitivity of the requisite pressure measurements. At the same time, the cross-sectional area of annulus A remains constant up until proximal neck 56 of balloon D is mounted to the inner surface 58 of outer body member B. By maintaining the cross-sectional area of annulus A as large as possible, the resistance experienced by doctor or a technician in inflating balloon D is kept to a minimum.

FIG. 3 represents an alternative mounting of the proximal end of the balloon to the distal end 60 of outer body member B. As shown in FIG. 3 the balloon inner surface 28 is mounted to the outer surface 66 of outer body member B adjacent its distal end 60. A vent lumen 68 is provided within the wall of outer body member B. As seen in FIG. 3, by providing vent lumen 68 in the wall of outer body member B, the cross-sectional areas of lumen 12 or annulus A remain uneffected. The presence of vent lumen 68 extending longitudinally into cavity 24 from proximal end of the catheter C (not shown) facilitates the purging of entrained gases within the balloon prior to insertion of the catheter C within the body. In order to use the catheter C, the entrained gases are purged from cavity 24 as well as annulus A by the injection of a contrast fluid. The contrast fluid (not shown) is injected with a syringe into annulus A. The contrast fluid flows into cavity 24 which is in flow communication with annulus A. By holding the distal end 18 of the catheter C in a vertical position with the tip T pointing towards the ground, and by further withdrawing the plunger of the syringe injecting the contrast fluid, the air or other entrained gases within cavity 24, due to the vacuum resulting from the withdrawal of the plunger (not shown) is drawn from cavity 24 through annulus A and out of the catheter C. The vent lumen 68 in the design of FIG. 3 further facilitates the purging of entrained gases. Experience has shown that with a proper amount of care, the entrained gases can also be effectively removed from cavity 24 without the use of vent lumen 68. However, the presence of lumen 68 streamlines the procedure.

Although inner body member I and tip T have been shown with a unitary lumen 12 and 14, respectively, alternate constructions are within the purview of the invention. For example, inner body member I and tip T can have two aligned lumens. The first lumen accommodates a guide wire and/or a guiding catheter and is used to measure pressure through the catheter C in the zone distal to the stenosis. The adjacent lumen which is substantially parallel to the initial lumen can be used to infuse oxygenated blood and other fluids distal to the balloon. The infusion lumen 70 preferably exits radially from tip T proximal to the distal end of tip T as shown in FIG. 6. Lumen 70 may also exit at an acute angle to the longitudinal axis of tip T.

As seen in FIG. 3, tip T can be further constructed to have a reducing taper 72 to further reduce the cross-sectional area tip adjacent its most distal end 74. In order to aid the performance of the angioplasty procedure, tip T can be made of a radiopaque material to allow close monitoring of its axial position in the arterial system of the body.

An alternative embodiment of the catheter C of the present invention is illustrated in FIGS. 6 through 9. In this embodiment, the catheter C features an elongated body E having a proximal segment 82 and a distal segment 84 with a tapered transition 86 therebetween. Elongated body E has at least one lumen extending therethrough from proximal segment 82 through distal segment 84. As shown in FIGS. 6 and 7, in one embodiment of the catheter C, elongated body E has three lumens 88, 90 and 92 extending longitudinally therethrough. Lumen 88 is aligned with tip lumen 14 (FIG. 6). A guide passes through aligned lumens 88 and 14. Lumen 90 is aligned with infusion lumen 70 of tip T for injection of drugs or oxygenated blood as necessary during the angioplasty procedure. As shown in FIG. 6, lumen 70 preferably exits acutely to radially from tip T proximally to its most distal end 74. Lumen 92 is a balloon inflation lumen which extends longitudinally through elongated body E and emerges into balloon cavity 94 adjacent its distal end 96. The proximal neck 56 of balloon D is secured along the balloon inner surface 28 to the outer surface 98 of elongated body E distally to taper transition 86. The distal neck 32 of balloon D can be secured to elongated body or tip T in the manner shown in FIG. 6 or as previously described with regard to FIGS. 2 or 4. To obtain the lowest possible profile of catheter C for the embodiment employing elongated body E, it is preferred to use the mounting method illustrated in FIGS. 2 or 4 to secure the distal neck 32 of balloon D in the distal end 18 of the catheter C. The previous discussion regarding variation of material hardnesses and tip and balloon lengths with regard to the embodiment illustrated in FIGS. 1 through 3 is also applicable to the alternative embodiment employing elongated body E. Similarly, the characteristics of tip T can be varied to include a reduction taper 72 as shown in FIG. 3 or the addition of a coil spring 80 embedded adjacent the most distal end 74 of the tip T. The tip T of the embodiment employing elongated body E can also be made from a radiopaque material to aid in tracing the progress of the catheter C within the artery in question.

Tip T can be produced from an elastometric polymeric material such as certain grades of nylon copolymers or the like.

Figure 9:
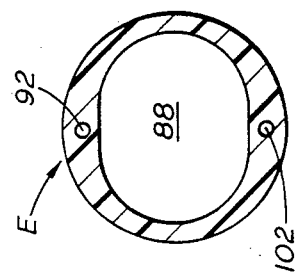
FIG. 9 is a section through lines 9—9 of FIG. 8.

Inflation and deflation means F encompasses balloon inflation lumen 92 which is in fluid communication with balloon cavity 94 adjacent its distal end 96. When using the catheter of the embodiment employing elongated body E, the balloon cavity 94 is filled with a contrast fluid before the catheter is inserted into the body of the patient. To facilitate removal of entrained air within balloon cavity 94, the doctor or technician aligns the distal end 18 of the catheter C in a vertical position with the tip T pointing upwardly. A syringe (not shown) is connected to the proximal end of lumen 92 whereupon pressure on the syringe plunger pushes contrast fluid upwardly through lumen 92 whereupon the contrast fluid falls downwardly within balloon cavity 94 towards its proximal end 100. At the same time entrained gas, usually air, percolates through lumen 92 to allow contrast fluid to enter balloon cavity 94. To facilitate the removal of the entrained gas within balloon cavity 94, the plunger on the contrast fluid injection needle is withdrawn thereby creating a vacuum adjacent the distal end 96 of balloon cavity 94 thereby withdrawing the gas entrained therein. Alternatively, in order to further facilitate the filling of balloon cavity 94 with contrast fluid, FIG. 9 illustrates the cross-section of elongated body E illustrating lumen 88 as well as balloon inflation lumen 102 and balloon vent lumen 92. In employing the combination of inflation lumen 102 and vent lumen 92, it is desirable to have inflation lumen 102 enter into balloon cavity 94 adjacent its proximal end 100 and vent lumen 92 enter balloon cavity 94 adjacent its distal end 96. When a technician or doctor aligns the catheter C in a vertical position with tip T pointing upward, contrast fluid can enter balloon cavity 94 through lumen 102 adjacent the proximal end and gradually displace entrained gas toward lumen 92 for removal from the catheter C. As soon as contrast fluid emerges from the proximal end (not shown) of lumen 92 the doctor or technician knows that the entire balloon cavity 94 is full of contrast fluid. It should be noted that the embodiment shown in FIG. 8 can be used with lumen 90 for infusion of drugs, as well as lumen 88, and balloon inflation and vent lumens 102 and 92 respectively.

Figure 10:
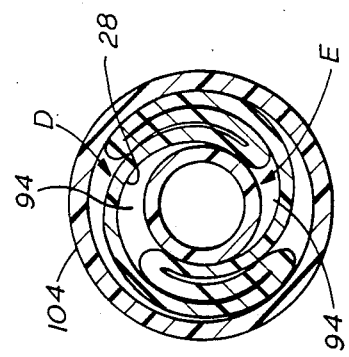
FIG. 10 is a sectional elevational view through the balloon showing the sleeve.
Figure 11:
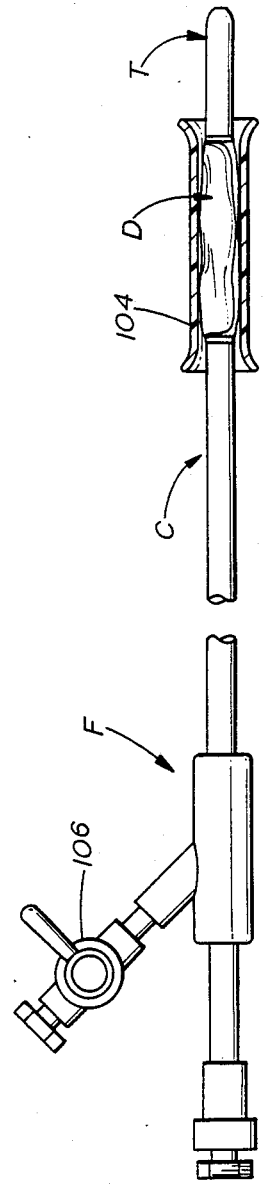
FIG. 11 is a elevational view of the catheter showing the sleeve over the balloon.

In the past, manufacturers have provided angioplasty catheters with the balloon wing folded as illustrated in FIG. 10. Wing folding is the technique of using digital manipulation or a machine to grab balloon D above and below elongated body E and in effect fold the balloon into a pair of winglike segments above and below elongated body E. These two wing segments are folded over elongated body E as shown in FIG. 10. However, when a doctor or technician performs the filling of balloon cavity 94 in the operating room prior to the angioplasty procedure, in order to properly fill balloon cavity 94 with contrast fluid, the wing folds must be undone thereby losing the advantage of the tendency of the balloon D to remain in the wing folded position. In order to take advantage of the tendency of the balloon D to remain in the wing folded position so as to maintain the lowest possible profile for insertion of the catheter C, the apparatus of the present invention incorporates a sleeve 104 which is adapted to be fitted over balloon D as shown in FIG. 10. In the apparatus of the present invention, the balloon cavity 94 is filled with contrast fluid in the factory and wing folded carefully by suitably designed machines. The sleeve 104 is fitted over the wing folded balloon which has already been filled with contrast fluid. The wing folding will displace some fluid from cavity 94. As shown in FIG. 11, the sleeve 104 is fitted over the entire balloon D and retains balloon D in a wing folded position. In order to prevent escape of the contrast fluid, the assembly of the catheter C is provided with a valve 106. The entire assembly is then sterilized so that it is ready for insertion into the body when unpackaged. In order to use the apparatus of the present invention employing sleeve 104, the doctor simply removes sleeve 104. With balloon cavity 94 already full of contrast fluid, the maintenance of sleeve 104 over the wing folded balloon D during shipping, acts to retain the balloon D in a wing folded position even after sleeve 104 is removed. When the catheter is properly inserted, by known means, additional contrast fluid can be added to inflate balloon B through balloon inflation lumen 92 (FIG. 8). It should be noted that the same benefits are available in the embodiment of the catheter C employing inner body member I and outer body member B except that the balloon is expanded by adding additional contrast fluid through annulus A after removing sleeve 104 and inserting the catheter C into the body. In order to deflate the balloon, valve 106 is opened thereby relieving the pressure within balloon cavity 94 and deflating the balloon.

The catheter C of the present invention provides advantages over known catheters. By using a soft tip, there is a reduced tendency of an overly stiff catheter pulling out the guiding catheter and/or guide wire from a stenosis when the angioplasty catheter C is advanced through a tortious arterial passage. The low profile of the distal end 18 of the catheter C further permits blood flow to the stenotic area as opposed to prior larger profile design catheters. The mounting of tip T wherein tip T is secured to the catheter body on several surfaces further improves the safety and operational features of the catheter in that the risk of dislodging of tip T is greatly reduced. The catheter C of the present invention provides a low profile distal end 18 with a larger profile proximal end so that dynamic measurements of pressure distal to the stenosis are uneffected by the guiding catheter or guide wire passing through the measuring lumen of the catheter C. The design of the present invention employs the advantage of a low profile distal end 18 with a larger profile proximal end thereby eliminating any need to remove the guide wire to obtain the appropriate response to dynamic pressure measurements necessary during the angioplasty procedure. The use of an additional lumen aids in blood and drug infusion and facilitates distal pressure measurements while maintaining a low catheter profile. In the embodiment employing inner body member I and outer body member B, the mounting of the proximal neck 56 of balloon D to the inner surface of outer body member B further aids in reducing the profile of the catheter when the balloon D is deflated. Prefilling of the balloon cavity 94 (FIG. 8) or cavity 24 (FIG. 2) with contrast fluid as well as wing folding and insertion of sleeve 104 allows the doctor to insert the catheter in a condition wherein balloon D retains its low profile shape due to the wing folding.

The Catheter C of the present invention has a soft tip T which extends from the most distal end point 74 (FIG. 3) to a point adjacent to the distal neck 32 of balloon D. The soft tip T is juxtaposed adjacent to the distal end 10 of inner body member I (FIG. 3). The soft tip T reduces the tendency of an overly stiff catheter to pull out the guiding catheter from the coronary artery ostium and/or pull the guidewire from the stenosis when the angioplasty catheter C is advanced through a tortuous arterial passage. At the same time the distal end 10 of the inner body member I being relatively stiffer than the tip T provides the necessary rigidity for precise placement of the balloon D within the stenosis. Additionally, the relative stiffness of distal end 10 under Balloon D resists constriction of lumen 12 due to hydrostatic pressures exerted by an inflated balloon D. The resistance to lumen construction is achieved in the catheter design as shown in FIGS. 1 or 8, for example.

One of the problems associated with catheters in prior use is the need to obtain accurate dynamic measurements of arterial pressure upstream and downstream of balloon D during inflation and after deflating of the balloon. The system previously employed is illustrated in FIG. 12. As seen in FIG. 12, there is a schematic representation of the angioplasty catheter C. A terminal fitting 200 includes a connection 202 and a transducer 204 which converts the upstream pressure, at a position indicated by arrow 206 to an electrical signal which shows the pressure on recorder 208. Similarly, another terminal fitting 210 allows fluid communication with the pressure in the artery 212 distal to balloon D. Arrow 214 represents a point at which the arterial pressure is measured downstream of balloon D through a fluid connection through terminal fitting 210. Transducer 216 converts the pressure measured at a point indicated by arrow 214.

In the past, several problems were encountered in using the pressure measurement system illustrated in FIG. 12. Frequently, to facilitate the use of the catheter C, the lead lines 218 and 220 were fairly lengthy. Lead lines 218 and 220 were frequently made from soft, compliant materials, which tended to affect dynamic pressure readings at the points indicated by arrows 214 and 206. Additionally, during the angioplasty procedure, blood or contrast media must be injected into connections 202 and/or 222 which requires temporary disconnection of the tubes.

In the past, prior to insertion of the catheter, the long lead lines 218 and 220 had to be flushed with a fluid to purge all air from such lines. Additionally, when blood or contrast media have to be injected through connections 202 or 222, such injection took place through fittings in lines 218 and 220. As the connections were temporarily removed during injection of blood or contrast media, entrapment of air into lines 218 and 220 was a potential problem. Thus, the doctor had to take time to insure that air was eliminated from lines 218 and 220 prior to connecting the lines 218, and 220 back to the catheter.

The length of leads 218 and 220 coupled with the compliant wall of such lines also affected the sensitivity of dynamic pressure readings seen on the recorder 208.

FIG. 13 illustrates an improvement over the prior pressure measurement system shown in FIG. 12. As seen in FIG. 13, the guiding catheter 224 is equipped with a pressure transducer 226 mounted to its hub or adjoining "Y" connector and having a sensor exposed to the arterial pressure upstream of balloon D at a point illustrated by arrow 206. Transducer 226 can also be mounted to the body of catheter C without departing from the spirit of the invention. The angioplasty catheter C having the construction illustrated in FIGS. 1 or 8, by example, and not by way of limitation, has a transducer 228 mounted to the hub or "Y" connector of the PTCA catheter or alternatively, embedded in its wall with a sensing element exposed to the arterial pressure downstream of balloon D at a point indicated by arrow 214. Suitable wires, emerge through fittings 200 and 210, respectively. Wires 230 and 232 are then connected to recorder 208 to give a visual readout of the pressure between two points, upstream and downstream of the inflated balloon D.

The inaccuracies in pressure measurement experienced by the system illustrated in FIG. 12 and described above, are eliminated in favor of a more sensitive system, which more accurately tracks the pressure proximally and distally of balloon D during inflation. Additionally, with the system as illustrated in FIG. 13, connections such as 222 or 202 can be closely mounted to terminal fittings 210 and 200 respectively so that drugs or blood can be infused with minimal risks of introduction of air into the catheter.

Another aspect of the invention is perfusion of blood distally of an inflated balloon to reduce ischemic reactions downstream of the balloon. By perfusing blood, preferably from the renal vein of the patient during balloon inflation, ischemic manifestations during prolonged coronary dilations of the balloon D are adequately suppressed. Hemoperfusion allows a more adequate and more durable remolding (dilation) of coronary plaque during angioplasty. A suitable blood withdrawal apparatus is connected to the renal vein (not shown) and through a blood pump is directed into connection 222 as represented by arrow 234. Renal blood is preferred due to its high oxygen content. Using perfusion of renal blood, allows the balloon inflation time to be extended to five minutes or more. Without distal hemoperfusion, patients can experience chest pain and electrocardiographic signs of progressive significant ischemia at a period of over 60 seconds balloon inflation. In the past, only poor flow rates were achieveable through coronary dilation catheters. And as most PTCA procedures could be performed without myocardial protection for 60 second balloon inflations, efforts to provide distal perfusion were abandoned. In a 1984 article in the Journal of the American College of Cardiology, Meier and Gruentzig, in an article entitled "Percutaneous Arterial Perfusion of Acutely Occluded Coronary Arteries in Dogs", described an experimental canine model in which a roller pump was used for as long as 150 minutes allowing flows of up to 100 ml/min. The incidence of hemolysis and thrombosis was considered unacceptable. Other experiments involved selective injection of exogenous fluids for distal coronary perfusion during PTCA. Fluorocarbon emulsions were mildly successful in reducing ischemic manifestations during balloon inflation but were associated with a high incidence of ventricular fibrillation.

Experiments have shown that with existing catheters available in the U.S. market, manufactured by USCI, inflated up to ten atmospheres, pressures of 50 to 75 psi were sufficient to yield blood flow rates of 40 to 60 ml/min. The inflation of the balloon, at certain times, however causes collapsing of the lumen of the catheter. Other commercially available catheters, such as those made by the ACS Company, however required pressures as high as 250 to 270 psi to achieve the same flow rates. Infusion of 40 to 60 ml/min. of blood allows for adequate suppression of ischemic manifestations of left anterior descending coronary arterial occlusions.

Relatively long term sub-selective coronary hemoperfusion can be used with patients with accute or impending myocardial infarction whether PTCA related or not. Such long term applications require catheters having as low as possible a resistance to blood flow along with automatic pumping equipment to provide reliable flows for prolonged periods. The resulting improvements in regional coronary blood flow would be immediate and dramatic. Chest pain would be reduced or eliminated, ST-T segment changes would be reduced or normalized. The patient's hemodynamic status and rhythm would also be stabilized. The use of long term hemoperfusion would offer patients the hope of undergoing angioplasty and/or surgery under semi-elective conditions. The use of oxygen rich renal blood allows for use of lower flow rates to prevent ischemia while being a low risk and non complicated method for withdrawal of blood as compared to use of arterial blood from a femoral artery. Thus lower pump pressures can be used with a properly designed catheter. Damage to the blood due to high operating pressures is reduced. Contamination or other complication which can arise by using a foreign blood as a source of the perfused blood is greatly reduced if not eliminated.

In order to facilitate distal hemoperfusion with blood having hemocrit levels of about 30-50%, it is desirable to reduce the resistance to blood flow through lumen 12 (see FIG. 1). To that end, it is desirable to maintain the following ratios:

$L_1$ = The length given by arrow 244 in inches
$L_2$ = The length given by arrow 248 in inches
$D_1$ = The lumen inside diameter given by arrow 242
$D_2$ = The lumen inside diameter given by arrow 246

$$\frac{L_1}{D_1^4} \leqq K \frac{L_2}{D_2^4}$$

K ranges from about 2-4 for blood having a 30-50% hemocrit level.

It has also been found that a specific dimensional relationship between the diameters of lumen 12, in the positions of arrows 16 and 22, as well as the length of the distal end of the catheter (measured from tapered segments 20 and 64 to the distal tip 74) and the length of the catheter proximally to transitions 20 and 64, provides optimal conditions to facilitate distal perfusion at reduced resistance to flow.

The variables just described are identified in FIG. 16. The inside diameter $D_1$ of lumen 12 is indicated by arrow 242. The length $L_1$ is represented by arrow 244.

The diameter $D_2$ of lumen 12 is represented by arrow 246. The length $L_2$ of the distal segment of lumen 12 represented by arrow 248.

For human whole blood of Hemocrit level of 30-50% the dimensional relationships yielding the lowest pressure drop for catheters configured as shown in FIGS. 8 or 16 is:

$$\Delta P(PSI) = Q5.2 \times 10^{-10} \left( \frac{L_1}{D_1^4} + \frac{L_2}{D_2^4} \right)$$

The FIG. $5.2 \times 10-10$ a constant for the blood as described above and includes a factor for justifying the units on both sides of the equation. Different values for this constant are used for other fluids. Q is the flow rate in cubic inches per min.

Another improvement over angioplasty catheters previously in use is illustrated in FIG. 14. PTCA catheters of known constructions or of the types illustrated in FIGS. 1 or 8, can be employed with the multi-stage balloon D illustrated in FIG. 14. The balloon may be formed to have two stages as illustrated in FIG. 14 or a multitude of stages as desired. The advantage of using a multi-staged balloon is that the same catheter can be used to remold or dilate coronary plaque during angioplasty without the necessity of having to remove one catheter and inserting another having a larger balloon capable of dilating the plaque further than the prior catheter. Thus, in operation, as shown in FIG. 14, the initial dilation of the plaque is done by placement the smaller stage 236 of the balloon D in the stenosis and dilating the plaque. The balloon D is then deflated and inserted further into the stenosis so that the distal stage 238 is inserted into the stenosis. The balloon is then reinflated for further dilation of the coronary plaque. The ratios between the stages can be made to vary depending upon the anticipated application. The balloon can be provided with two stages or more, as desired, depending on the application.

The dotted circle labeled 15 in FIG. 14 is illustrated in the section shown in FIG. 15. FIG. 13, illustrates a coating of the entire catheter especially the balloon, with a combination silicone type 4159 from Dow Corning Company and heparin layer 240 as illustrated in FIG. 15. The silicone adds to the lubricity of the catheter C and the heparin prevents the formation of clots. Heparin is interstitially placed within the silicone matrix and then made to adhere to the catheter C walls including the balloon D. Prior applications involved heparin coated catheters in combination with a polymer which did not provide lubricity. The combination of silicone and heparin yields both advantages simultaneously. The catheter is plasma treated in order to obtain a suitable bond of the silicone/heparin layer to the catheter material, which by example and not by way of limitation may be polyethylene.

The foregoing disclosure and description of the invention are illustrative and explanatory thereof, and various changes in the size, shape and materials, as well as in the details of the illustrated construction may be made without departing from the spirit of the invention.

We claim:

1. A low profile catheter for dilating stenotic lesions in the vascular system and other body cavities, insertable over a guide comprising:

an elongated body having a proximal and distal segment, said body defining at least one lumen extending therethrough;

an elongated tip segment connected adjacent to the distal end of said distal segment of said body, said tip defining at least one substantially smooth bore lumen therethrough, said lumen in said body in flow communication with said lumen in said tip thereby allowing the catheter to be advanced over a guide extending through said lumen in said body in said tip;

said body being made of a harder material than the material of said tip;

a balloon mounted in close proximity to the outer surface of said distal segment of said body defining a balloon cavity therebetween, said balloon having a proximal and distal neck, said balloon disposed substantially proximally to said tip, juncture means for providing a transition between said tip and said distal segment of said body, said distal neck of said balloon mounted adjacent to the juncture between said elongated tip segment and said distal end of said distal segment of said body;

said proximal neck of said balloon mounted to said elongated body;

said distal segment of said body being substantially nondistensible as the balloon is inflated to substantially its full normal operating inflation pressure; and means within said body for selectively inflating and deflating said balloon through said cavity.

2. The catheter of claim 1 wherein:

the proximal end of said tip has an adjacent internal mounting shoulder circumscribing said lumen extending therethrough;

said shoulder is mounted to the distal end of said distal segment of said body; and the distal neck of said balloon is connected directly onto the outer surface of said distal segment of said body adjacent to the proximal end of said tip whereupon the outer surface of the distal neck of said balloon is substantially longitudinally aligned with the outer surface of said tip.

3. The catheter of claim 1 wherein:

the proximal end of said tip has an adjacent internal mounting shoulder circumscribing said lumen extending therethrough;

said shoulder is mounted to the distal end of said distal segment of said body; and said tip further comprising:

an external mounting shoulder adjacent its proximal end; and said distal neck of said balloon is connected to said external shoulder whereupon the outer surface of the distal neck of said balloon is substantially aligned with the outer surface of said tip adjacent the proximal end of said tip.

4. The catheter of claim 3 wherein said inner shoulder further comprises:

an annular surface; and a radial surface adjacent one end of said annular surface;

said annular and radial surfaces of said shoulder connected to said distal end of said distal segment.

5. The catheter of claim 1 wherein:

said tip is mounted to the distal extremity of said body thereby defining a joint therebetween;

said tip having an outer surface substantially in longitudinal alignment with the outer surface of said distal segment of said body;

said distal neck of said balloon is mounted over said aligned outer surface.

6. The catheter of claim 5 further comprising:

a tapered transitional segment extending from the distal end of the outer surface of said distal neck of said balloon to the outer surface of said tip.

7. The catheter of claim 1 wherein:

said tip further comprises at least one taper between its proximal and distal ends;

said tip has an overall length in the range of about 1-30 mm;

said tip is formed of a soft elastomeric polymeric material.

8. The catheter of claim 1 wherein:
said tip is formed with a radiopaque filler.

9. The catheter of claim 1 wherein:

said tip further includes a coil spring embedded into said tip adjacent its distal end, said spring having a longitudinal axis aligned with the longitudinal axis of said tip, said spring circumscribing said lumen in said tip receiving the guide.

10. The catheter of claim 1 further comprising:

a tubular hold down sleeve, mounted to said balloon said sleeve adapted to be fitted substantially circumscribing said balloon to retain said balloon in a wing-folded position after said balloon has been substantially liquid filled, whereupon when said sleeve is removed, said balloon retains a low profile by retaining said wing-folds as the catheter is inserted into the vascular system or other body cavity.

11. The catheter of claim 1 wherein;

said balloon is formed having a plurality of stages of differing outside diameters when said balloon is inflated;

whereupon the same catheter can be used to dilate a stenosis in progressively increasing dimensional increments.

12. The catheter of claim 1, further comprising:

a first pressure sensing element mounted to the body of the catheter, adjacent to proximal end of said catheter, distally to said balloon, said first element adapted to sense pressure in the vascular system or the patient's body cavity distally of said balloon during inflation and transmit a first electrical signal in relation thereto;

a second pressure sensing element mounted to the catheter, adjacent to proximal end of said catheter, said second element adapted to sense pressure in the vascular system or the patient's body cavity proximally of said balloon during inflation and transmit a second electrical signal in relation thereto;

signal conduction means mounted to the body of the catheter connected to said first and second pressure sensing elements for conducting said first and second electrical signals to the proximal end of the catheter located outside the patient's body.

13. The catheter of claim 1, further comprising:

connection means mounted in flow communication with said lumen in said body of the catheter on a first end and adapted to be connected to a blood supply source in the patient's vascular system on a second end, for selectively allowing perfusion of the patient's own blood during inflation of said balloon.

14. The catheter of claim 13, further comprising:

pump means mounted to said connection means for overcoming resistance to flow within said connection means and said lumen.

15. The catheter of claim 13, wherein:

said second end of said connection means is adapted to be connected to a blood supply source coming from the renal vein of the vascular system.

16. The catheter of claim 15, wherein: lumen cross-sectional area in said inner body member proximate to said tapered segment thereon;

a balloon, said balloon having a proximal neck connected to said outer body member adjacent the distal end of said outer body member;

said balloon having a distal neck connected in close proximity to the outer surface of said distal end of said inner body member; and said balloon defining an annular cavity extending from and in flow communication with said annulus and terminating adjacent said distal end of said inner body member.

17. The catheter of claim 1, comprising:

a coating of at least a portion of the exterior of the catheter coming in contact with the patient comprising of a combination of a lubricating material and an anti-clotting material.

18. The catheter of claim 17, wherein:

said lubricating material is silicone and said anti clotting material is heparin.

19. The catheter of claim 18, wherein:

the catheter is plasma treated to improve the bonding of the silicone and heparin coating.

20. A low profile catheter for dilating stenotic lesions in the vascular system and other body cavities, insertable over a guide comprising:

a tubular outer body member;

a tubular inner body member disposed substantially within said outer body member thereby defining an annulus therebetween;

said inner body member having a distal end extending beyond the distal end of said outer body member;

said inner body member defining at least one lumen extending therethrough;

an elongated tip segment connected adjacent to the distal end of said inner body member, said tip defining at least one substantially smooth bore lumen therethrough, said lumen in said inner body member in flow communication with said lumen in said tip thereby allowing the catheter to be advanced over a guide extending through said lumen in said inner body member and said tip;

said inner body member being made of a harder material than the material of said tip;

a balloon, said balloon having a proximal neck extending from and connected to said outer body member adjacent to distal end of said outer body member;

said balloon having a distal neck extending to and connected in close proximity to the outer surface of said distal end of said inner body member and substantially proximally of said elongated tip segment;

said distal end of said inner body member being substantially nondistensible as the balloon is inflated to substantially its fully operating inflation pressure; and said balloon defining an annular cavity extending from and in flow communication with said annulus and terminating proximally of said tip.

21. The catheter of claim 20 wherein;

said balloon is formed having a plurality of stages of differing outside diameters when said balloon is inflated;

whereupon the same catheter can be used to dilate a stenosis in progressively increasing dimensional increments.

22. The catheter of claim 20, further comprising:

a first pressure sensing element mounted to the catheter, adjacent to proximal end of said catheter, said first element adapted to sense pressure in the vascular system or the patient's body cavity distally of said balloon during inflation and transmit a first electrical signal in relation thereto;

a second pressure sensing element mounted to the catheter, adjacent to proximal end of said catheter, said second element adapted to sense pressure in the vascular system or the patient's body cavity proximally of said balloon during inflation and transmit a second electrical signal in relation thereto;

signal conduction means mounted to the inner and outer body members of the catheter connected to said first and second pressure sensing elements for conducting said first and second electrical signals to the proximal end of the catheter located outside the patient's body.

23. The catheter of claim 20, further comprising:

connection means mounted in flow communication with said lumen in said inner body member of the catheter on a first end and adapted to be connected to a blood supply source in the patient's vascular system on a second end for selectively allowing perfusion of the patient's own blood during inflation of said balloon.

24. The catheter claim 23, further comprising:

pump means mounted to said connection means for overcoming resistance to flow within said connection means and said lumen.

25. The catheter of claim 20, comprising:

a coating of at least a portion of the exterior of the catheter coming in contact with the patient comprising of a combination of a lubricating material and an anti-clotting material.

26. The catheter of claim 25, wherein:

said lubricating material is silicone and said anti clotting material is heparin.

27. The catheter of claim 26, wherein:

the catheter is plasma treated to improve the bonding of the silicone and heparin coating.

28. A catheter for dilating stenotic lesions in the vascular system and other body cavities, insertable over a guide comprising:

a tubular outer body member;

a tubular inner body member disposed substantially within said outer body member thereby defining an annulus therebetween;

said inner body member having a distal end extending beyond the distal end of said outer body member;

said inner body member defining at least one lumen extending therethrough;

an elongated tip segment connected adjacent to the distal end of said inner body member, said tip defining at least one lumen therethrough, said lumen in said inner body member in flow communication with said lumen in said tip thereby allowing the catheter to be advanced over a guide extending through said lumen in said inner body member and said tip;

said inner body member being harder than said tip;

a balloon, said balloon having a proximal neck connected to said outer body member adjacent the distal end of said outer body member;

said balloon having a distal neck connected in close proximity to the outer surface of said distal end of said inner body member;

said balloon defining an annular cavity extending from and in flow communication with said annulus and terminating adjacent said tip;

the proximal end of said tip having an adjacent internal mounting shoulder circumscribing said lumen extending therethrough;

said shoulder is mounted to the distal end of said inner body member;

the distal neck of said balloon is connected directly onto the outer surface of said distal end of said inner body member adjacent to the proximal end of said tip, whereupon the outer surface of the distal neck of said balloon is substantially longitudinally aligned with the outer surface of said tip adjacent its proximal end;

said proximal neck of said balloon is connected to the inner surface of said outer body member;

said outer body member is tapered adjacent its distal end;

said inner body member further comprises a tapered segment thereon, positioned adjacent to said tapered segment of said outer body member, thereby reducing the catheter profile at the distal end of said inner body member while permitting a larger lumen cross sectional area in said inner body member proximate to said tapered segment thereon.

29. The catheter of claim 28 wherein said inner body member and said tip are further formed having an infusion lumen extending therethrough said infusion lumen extending substantially parallel to said lumen receiving the guide.

30. the catheter of claim 28, wherein:

the length ($L_1$) of the catheter proximally to said taper divided by the inside diameter ($D_1$) of said lumen proximally to said taper taken to the fourth power is less than or equal to about 2–4 times the quotient of the length ($L_2$) of the catheter distally to said taper divided by the inside diameter ($D_2$) of said lumen distally of said taper taken to the fourth power.

31. A catheter for dilating stenotic lesions in the vascular system and other body cavities, insertable over a guide comprising:

a tubular outer body member;

a tubular inner body member disposed substantially within said outer body member thereby defining an annulus therebetween;

said inner body member having a distal end extending beyond the distal end of said outer body member;

said inner body member defining at least one lumen extending therethrough;

an elongated tip segment connected adjacent to the distal end of said inner body member, said tip defining at least one lumen therethrough, said lumen in said inner body member in flow communication with said lumen in said tip thereby allowing the catheter to be advanced over a guide extending through said lumen in said inner body member and said tip;
said inner body member being harder than said tip;
a balloon, said balloon having a proximal neck connected to said outer body member adjacent the distal end of said outer body member;
said balloon having a distal neck connected in close proximity to the outer surface of said distal end of said inner body member;
said balloon defining an annular cavity extending from and in flow communication with said annulus and terminating adjacent said tip;
the proximal end of said tip having adjacent internal mounting shoulder circumscribing said lumen extending therethrough;
said shoulder is mounted to the distal end of said inner body member; and
said tip further comprises:
an external mounting shoulder adjacent its proximal end;
said distal neck of said balloon is connected to said external shoulder, whereupon the outer surface of the distal neck of said balloon is substantially aligned with the outer surface of said tip adjacent the proximal end of said tip;
said proximal neck of said balloon is connected to the inner surface of said outer body member;
said outer body member is tapered adjacent its distal end;
said inner body member further comprises a tapered segment thereon, positioned adjacent to said tapered segment of said outer body member, thereby reducing the catheter profile at the distal end of said inner body member while permitting a larger lumen cross sectional area in said inner body member proximate to said tapered segment thereon.

32. The catheter of claim 31 wherein said inner body member and said tip are further formed having an infusion lumen extending therethrough said infusion lumen extending substantially parallel to said lumen receiving the guide.

33. The catheter of claim 31, wherein:
the length ($L_1$) of the catheter proximally to said taper divided by the inside diameter ($D_1$) of said lumen proximally to said taper taken to the fourth power is less than or equal to about 2-4 times the quotient of the length ($L_2$) of the catheter distally to said taper divided by the inside diameter ($D_2$) of said lumen distally of said taper taken to the fourth power.

34. A catheter for dilating stenotic lesions in the vascular system and other body cavities, insertable over a guide comprising:
a tubular outer body member;
a tubular inner body member disposed substantially within said outer body member thereby defining an annulus therebetween;
said inner body member having a distal end extending beyond the distal end of said outer body member;
said inner body member defining at least one lumen extending therethrough;
an elongated tip segment connected adjacent to the distal end of said inner body member, said tip defining at least one lumen therethrough, said lumen in said inner body member in flow communication with said lumen in said tip thereby allowing the catheter to be advanced over a guide extending through said lumen in said inner body member and said tip;
said inner body member being harder than said tip;
a balloon, said balloon having a proximal neck connected to said outer body member adjacent the distal end of said outer body member;
said balloon having a distal neck connected in close proximity to the outer surface of said distal end of said inner body member;
said balloon defining an annular cavity extending from and in flow communication with said annulus and terminating adjacent said tip;
said tip is mounted to the distal extremity of said inner body member thereby defining a joint therebetween;
said tip having an outer surface substantially in longitudinal alignment with the outer surface of said distal end of said inner body member;
said distal neck of said balloon is mounted over said aligned outer surfaces;
said proximal neck of said balloon is connected to the inner surface of said outer body member;
said outer body member is tapered adjacent its distal end; and
said inner body member further comprises a tapered segment thereon, positioned adjacent to said tapered segment of said outer body member, thereby reducing the catheter profile at the distal end of said inner body member while permitting a larger lumen cross sectional area in said inner body member proximate to said tapered segment thereon.

35. The catheter of claim 34 wherein said inner body member and said tip are further formed having an infusion lumen extending therethrough said infusion lumen extending substantially parallel to said lumen receiving the guide.

36. The catheter of claim 34, wherein:
the length ($L_1$) of the catheter proximally to said taper divided by the inside diameter ($D_1$) of said lumen proximally to said taper taken to the fourth power is less than or equal to about 2-4 times the quotient of the length ($L_2$) of the catheter distally to said taper divided by the inside diameter ($D_2$) of said lumen distally of said taper taken to the fourth power.

37. The catheter of claim 28, 31 or 34 wherein:
said annulus has a substantially constant cross sectional area, proximately and distally adjacent said tapered segment on said inner body member.

38. The catheter of claim 37 wherein:
the distal extremity of said outer body member is tapered down to meet the outer surface of said proximal neck of said balloon.

39. A catheter for dilating stenotic lesions in the vascular system and other body cavities, insertable over a guide comprising:
a tubular outer body member;
a tubular inner body member disposed substantially within said outer body member thereby defining an annulus therebetween;
said inner body member having a distal end extending beyond the distal end of said outer body member;
said inner body member defining at least one lumen extending therethrough;
an elongated tip segment connected adjacent to the distal end of said inner body member, said tip defining at least one lumen therethrough, said lumen in said inner body member in flow communication with said lumen in said tip thereby allowing the catheter to be advanced over a guide extending through said lumen in said inner body member and said tip;

said inner body member being harder than said tip;

said outer body member is tapered adjacent its distal end;

said inner body member further comprises a tapered segment thereon, positioned adjacent to said tapered segment of said outer body member, thereby reducing the catheter profile at the distal end of said inner body member while permitting a larger lumen cross sectional area in said inner body member proximate to said tapered segment thereon;

a balloon, said balloon having a proximal neck connected to said outer body member adjacent the distal end of said outer body member;

said balloon having a distal neck connected in close proximity to the outer surface of said distal end of said inner body member; and said balloon defining an annular cavity extending from and in flow communication with said annulus and terminating adjacent said tip.

40. The catheter of claim 39 wherein;

said balloon is formed having a plurality of stages of differing outside diameters when said balloon is inflated;

whereupon the same catheter can be used to dilate a stenosis in progressively increasing dimensional increments.

41. The catheter of claim 39, further comprising:

a first pressure sensing element mounted to the catheter, said first element adapted to sense pressure in the vascular system or the patient's body cavity distally of said balloon during inflation and transmit a first electrical signal in relation thereto;

a second pressure sensing element mounted to the catheter, said second element adapted to sense pressure in the vascular system or the patient's body cavity proximally of said balloon during inflation and transmit a second electrical signal in relation thereto;

signal conduction means mounted to the inner and outer body members of the catheter connected to said first and second pressure sensing elements for conducting said first and second electrical signals to the proximal end of the catheter located outside the patient's body.

42. The catheter of claim 39, further comprising:

connection means mounted in flow communication with said lumen in said inner body member of the catheter on a first end and adapted to be connected to a blood supply source in the patient's vascular system on a second end, for selectively allowing perfusion of the patient's own blood during inflation of said balloon.

43. The catheter claim 42, further comprising:

pump means mounted to said connection means for overcoming resistance to flow within said connection means and said lumen.

44. The catheter of claim 42, wherein:

said second end of said connection means is adapted to be connected to a blood supply source coming from the renal vein of the vascular system.

45. The catheter of claim 39, comprising:

a coating of at least a portion of the exterior of the catheter coming in contact with the patient comprising of a combination of a lubricating material and an anti-clotting material.

46. The catheter of claim 45, wherein:

said lubricating material is silicone and said anti clotting material is heparin.

47. The catheter of claim 46, wherein:

the catheter is plasma treated to improve the bonding of the silicone and heparin coating.

48. The catheter of claim 39, wherein:

the length ($L_1$) of the catheter proximally to said taper divided by the inside diameter ($D_1$) of said lumen proximally to said taper taken to the fourth power is less than or equal to about 2-4 times the quotient of the length ($L_2$) of the catheter distally to said taper divided by the inside diameter ($D_2$) of said lumen distally of said taper taken to the fourth power.

49. A low profile catheter for dilating stenotic lesions in the vascular system and other body cavities, insertable over a guide comprising:

an elongated body having a proximal and distal segment, said body defining at least one lumen extending therethrough;

an elongated tip segment connected adjacent to the distal end of said distal segment of said body, said tip defining at least one substantially smooth bore lumen therethrough, said lumen in said body in flow communication with said lumen in said tip thereby allowing the catheter to be advanced over guide extending through said lumen in said body and said tip;

said body being harder than said tip;

a balloon mounted in close proximity to the outer surface of said distal segment of said body defining a balloon cavity therebetween, said balloon having a proximal and distal neck said balloon cavity disposed between said distal segment of said body and said portion of said balloon between said proximal and distal necks of said balloon, said distal neck of said balloon mounted adjacent to the juncture between said elongated tip segment and said distal end of said distal segment of said body;

means within said body for selectively inflating and deflating said balloon through said cavity;

the proximal end of said tip having an adjacent internal mounting shoulder circumscribing said lumen extending therethrough;

said shoulder is mounted to the distal end of said distal segment of said body;

the distal neck of said balloon is connected directly onto the outer surface of said distal segment of said body adjacent to the proximal end of said tip whereupon the outer surface of the distal neck of said balloon is substantially longitudinally aligned with the outer surface of said tip;

said distal segment of said body further comprises a tapered transition section for reducing the cross sectional area of said distal segment of said body to a smaller size than said proximal segment of said body, as measured in a plane perpendicular to the longitudinal axis of said body; and said balloon connected distally to said tapered transition such that the profile of the catheter does not exceed the cross-section of said proximal segment when said balloon is deflated.

50. The catheter of claim 49, wherein:

the length ($L_1$) of the catheter proximally to said taper divided by the inside diameter ($D_1$) of said lumen proximally to said taper taken to the fourth power is less than or equal to about 2-4 times the quotient of the length ($L_2$) of the catheter distally to said taper divided by the inside diameter ($D_2$) of said lumen distally of said taper taken to the fourth power.

51. A low profile catheter for dilating stenotic lesions in the vascular system and other body cavities, insertable over a guide comprising:

an elongated body having a proximal and distal segment, said body defining at least one lumen extending therethrough;

an elongated tip segment connected adjacent to the distal end of said distal segment of said body, said tip defining at least one substantially smooth bore lumen therethrough, said lumen in said body in flow communication with said lumen in said tip thereby allowing the catheter to be advanced over a guide extending through said lumen in said body and said tip;

said body being harder than said tip;

a balloon mounted in close proximity to the outer surface of said distal segment of said body defining a balloon cavity therebetween, said balloon having a proximal and distal neck, said balloon cavity disposed between said distal segment of said body and said portion of said balloon between said proximal and distal necks of said balloon, said distal neck of said balloon mounted adjacent to the juncture between said elongated tip segment and said distal end of said distal segment of said body;

means within said body for selectively inflating and deflating said balloon through said cavity;

the proximal end of said tip having an adjacent internal mounting shoulder circumscribing said lumen extending therethrough;

said shoulder is mounted to the distal end of said distal segment of said body;

said tip further comprising:

an external mounting shoulder adjacent its proximal end;

said distal neck of said balloon is connected to said external shoulder whereupon the outer surface of the distal neck of said balloon is substantially aligned with the outer surface of said tip adjacent the proximal end of said tip;

said distal segment of said body further comprises a tapered transition section for reducing the cross sectional area of said distal segment of said body to a smaller size than said proximal segment of said body, as measured in a plane perpendicular to the longitudinal axis of said body; and said balloon connected distally to said tapered transition such that the profile of the catheter does not exceed the cross-section of said proximal segment when said balloon is deflated.

52. The catheter of claim 51, wherein:

the length ($L_1$) of the catheter proximally to said taper divided by the inside diameter ($D_1$) of said lumen proximally to said taper taken to the fourth power is less than or equal to about 2-4 times the quotient of the length ($L_2$) of the catheter distally to said taper divided by the inside diameter ($D_2$) of said lumen distally of said taper taken to the fourth power.

53. A low profile catheter for dilating stenotic lesions in the vascular system and other body cavities, insertable over a guide comprising:

an elongated body having a proximal and distal segment, said body defining at least one lumen extending therethrough;

an elongated tip segment connected adjacent to the distal end of said distal segment of said body, said tip defining at least one substantially smooth bore lumen therethrough, said lumen in said body in flow communication with said lumen in said tip thereby allowing the catheter to be advanced over a guide extending through said lumen in said body and said tip;

said body being harder than said tip;

a balloon mounted in close proximity to the outer surface of said distal segment of said body defining a balloon cavity therebetween said balloon having a proximal and distal neck, said balloon cavity disposed between said distal segment of said body and said portion of said balloon between said proximal and distal necks of said balloon, said distal neck of said balloon mounted adjacent to the juncture between said elongated tip segment and said distal end of said distal segment of said body; and means within said body for selectively inflating and deflating said balloon through said cavity;

said tip is mounted to the distal extremity of said body thereby defining a joint therebetween;

said tip having an outer surface substantially in longitudinal alignment with the outer surface of said distal segment of said body;

said distal neck of said balloon is mounted over said aligned outer surfaces;

said distal segment of said body further comprises a tapered transition section for reducing the cross sectional area of said distal segment of said body to a smaller size than said proximal segment of said body, as measured in a plane perpendicular to the longitudinal axis of said body; and said balloon connected distally to said tapered transition such that the profile of the catheter does not exceed the cross-section of said proximal segment when said balloon is deflated.

54. The catheter of claim 53, wherein:

the length ($L_1$) of the catheter proximally to said taper divided by the inside diameter ($D_1$) of said lumen proximally to said taper taken to the fourth power is less than or equal to about 2-4 times the quotient of the length ($L_2$) of the catheter distally to said taper divided by the inside diameter ($D_2$) of said lumen distally of said taper taken to the fourth power.

55. The catheter of claim 49, 51 or 53 wherein:

said tube and said tip are further formed having an infusion lumen extending therethrough, said infusion lumen extending substantially parallel to said lumen receiving the guide.

56. The catheter of claim 55 wherein:

said infusion lumen terminates at an acute to a right included angle as measured between the longitudinal axis of said tip and said infusion lumen, said infusion lumen terminating proximally to the distal end of said tip.

57. The catheter of claim 56 wherein said inflation and deflation means further comprises:

at least one balloon lumen extending through said proximal and distal segments of said body and terminating adjacent said balloon cavity thereby permitting fluid flow through said body into said balloon cavity.

58. The catheter of claim 57 wherein:
said balloon lumen terminates adjacent the distal end of said balloon cavity.

59. The catheter of claim 57 comprising:
a first and second balloon lumens, said first balloon lumen adapted for filling said balloon cavity with an inflating liquid and said second balloon lumen adapted to carry entrained gas from the balloon cavity.

60. The catheter of claim 59 wherein:
said first lumen terminates adjacent the proximal end of said balloon cavity; and
said second lumen terminates adjacent the distal end of said balloon cavity.

61. The catheter of claim 60 wherein:
said tip further comprises at least one taper between its proximal and distal ends;
said tip has an overall length in the range of about 1-30 mm;
said tip is formed of a soft elastomeric polymeric material.

62. The catheter of claim 61 wherein:
said tip is formed with a radiopaque filler.

63. The catheter of claim 62 wherein:
said tip further includes a coil spring embedded into said tip adjacent its distal end, said spring having a longitudinal axis aligned with the longitudinal axis of said tip, said spring circumscribing said lumen in said tip receiving the guide.

64. The catheter of claim 63 further comprising:
a tubular hold down sleeve, mounted to said balloon said sleeve adapted to be fitted substantially circumscribing said balloon to retain said balloon in a wing-folded position after said balloon has been substantially liquid filled, whereupon when said sleeve is removed, said balloon retains a low profile by retaining said wing-folds as the catheter is inserted into the vascular system or other body cavity.

65. The catheter of claim 57 further comprising:
a tubular hold down sleeve, mounted to said balloon said sleeve adapted to be fitted substantially circumscribing said balloon to retain said balloon in a wing-folded position after said balloon has been substantially liquid filled, whereupon when said sleeve is removed, said balloon retains a low profile by retaining said wing-folds as the catheter is inserted into the vascular system or other body cavity.

66. The catheter of claim 39 wherein:
said tip further includes a coil spring embedded into said tip adjacent its distal end, said spring having a longitudinal axis aligned with the longitudinal axis of said tip, said spring circumscribing said lumen receiving the guide.

67. The catheter of claim 39 wherein:
said tip is formed with a radiopaque filler.

68. The catheter of claim 39 wherein:
said tip further comprises at least one taper between its proximal and distal ends;
said tip has an overall length in the range of about 1-30 mm;
said tip is formed of a soft elastomeric polymeric material.

69. The catheter of claim 39 wherein said inner body member and said tip are further formed having an infusion lumen extending therethrough said infusion lumen extending substantially parallel to said lumen receiving the guide.

70. The catheter of claim 69 wherein:
said infusion lumen terminates at an acute to a right included angle measured between the longitudinal axis of said tip and said infusion lumen, said infusion lumen terminating proximally to the distal end of said tip.

71. The catheter of claim 72 wherein:
said proximal neck of said balloon is connected to the outer surface of said outer body member;
said outer body member further comprising at least one bleed lumen disposed within the wall of said outer body member and extending longitudinally through it substantially through its length, said bleed lumen in flow communication with said annular cavity.

72. The catheter of claim 39 further comprising:
the proximal end of said tip has an adjacent internal mounting shoulder circumscribing said lumen extending therethrough;
said shoulder is mounted to the distal end of said inner body member;
the distal neck of said balloon is connected directly onto the outer surface of said distal end of said inner body member adjacent to the proximal end of said tip, whereupon the outer surface of the distal neck of said balloon is substantially longitudinally aligned with the outer surface of said tip adjacent its proximal end.

73. The catheter of claim 72 wherein:
said proximal neck of said balloon is connected to the inner surface of said outer body member.

74. The catheter of claim 73 wherein said inner body member and said tip are further formed having an infusion lumen extending therethrough said infusion lumen extending substantially parallel to said lumen receiving the guide.

75. The catheter of claim 74 wherein:
said infusion lumen terminates at an acute to a right included angle measured between the longitudinal axis of said tip and said infusion lumen, said infusion lumen terminating proximally to the distal end of said tip.

76. The catheter of claim 75 wherein:
said tip further comprises at least one taper between its proximal and distal ends;
said tip has an overall length in the range of about 1-30 mm;
said tip is formed of a soft elastomeric polymeric material.

77. The catheter of claim 76 wherein:
said tip is formed with a radiopaque filler.

78. The catheter of claim 77 wherein:
said tip further includes a coil spring embedded into said tip adjacent its distal end, said spring having a longitudinal axis aligned with the longitudinal axis of said tip, said spring circumscribing said lumen receiving the guide.

79. The catheter of claim 39 wherein;
the proximal end of said tip has an adjacent internal mounting shoulder circumscribing said lumen extending therethrough;
said shoulder is mounted to the distal end of said inner body member; and
said tip further comprises:
an external mounting shoulder adjacent its proximal end; and said distal neck of said balloon is connected to said external shoulder, whereupon the outer surface of the distal neck of said balloon is substantially aligned with the outer surface of said tip adjacent the proximal end of said tip.

80. The catheter of claim 79 wherein:

said proximal neck of balloon is connected to the outer surface of said outer body member;

said outer body member further comprising at least one bleed lumen disposed within the wall of said outer body member and extending longitudinally through it substantially through its length, said bleed lumen in flow communication with said annular cavity.

81. The catheter of claim 79 wherein said inner shoulder further comprises:

an annular surface; and a radial surface adjacent one end of said annular surface;

said annular and radial surfaces of said shoulder connected to said distal end of said inner body member.

82. The catheter of claim 39 wherein:

said tip is mounted to the distal extremity of said inner body member thereby defining a joint therebetween;

said tip having an outer surface substantially in longitudinal alignment with the outer surface of said distal end of said inner body member; and said distal neck of said balloon is mounted over said aligned outer surfaces.

83. The catheter of claim 82 further comprising:

a tapered transitional segment extending from the distal end of the outer surface of said distal neck of said balloon to the outer surface of said tip.

84. The catheter of claim 82 wherein:

said proximal neck of said balloon is connected to the outer surface of said outer body member;

said outer body member further comprising at least one bleed lumen disposed within the wall of said outer body member and extending longitudinally through it substantially through its length, said bleed lumen in flow communication with said annular cavity.

85. A catheter for dilating stenotic lesions in the vascular system and other body cavities, insertable over a guide comprising:

a tubular outer body member;

a tubular inner body member disposed substantially within said outer body member thereby defining an annulus therebetween;

said inner body member having a distal end extending beyond the distal end of said outer body member;

said inner body member defining at least one lumen extending therethrough;

said outer body member is tapered and adjacent its distal end;

said inner body member further comprises a tapered segment thereon, positioned adjacent to said tapered segment of said outer body member, thereby reducing the catheter profile at the distal end of said inner body member while permitting a larger lumen cross-sectional area in said inner body member proximate to said tapered segment thereon;

a balloon, said balloon having a proximal neck connected to said outer body member adjacent the distal end of said outer body member;

said balloon having a distal neck connected in close proximity to the outer surface of said distal end of said inner body member; and said balloon defining an annular cavity extending from and in flow communication with said annulus and terminating adjacent said distal end of said inner body member.

* * * * *